United States Patent
Vollero et al.

(10) Patent No.: US 10,047,437 B2
(45) Date of Patent: Aug. 14, 2018

(54) PROCESS GAS MANAGEMENT SYSTEM AND PHOTOIONIZATION DETECTOR

(71) Applicant: INFICON, Inc., East Syracuse, NY (US)

(72) Inventors: Michael F. Vollero, Manlius, NY (US); Shawn M. Briglin, Chittenango, NY (US)

(73) Assignee: INFICON, INC., East Syracuse, NY (US)

( * ) Notice: Subject to any disclaimer, the term of this patent is extended or adjusted under 35 U.S.C. 154(b) by 64 days.

(21) Appl. No.: 15/181,929

(22) Filed: Jun. 14, 2016

(65) Prior Publication Data

US 2016/0362787 A1 Dec. 15, 2016

Related U.S. Application Data

(60) Provisional application No. 62/175,771, filed on Jun. 15, 2015.

(51) Int. Cl.
*C23C 16/52* (2006.01)
*C23C 16/455* (2006.01)
*G01N 27/64* (2006.01)

(52) U.S. Cl.
CPC ........ *C23C 16/45544* (2013.01); *C23C 16/52* (2013.01); *G01N 27/64* (2013.01)

(58) Field of Classification Search
CPC ................................................ C23C 16/45544
See application file for complete search history.

(56) References Cited

U.S. PATENT DOCUMENTS

| | | | |
|---|---|---|---|
| 4,413,185 A | 11/1983 | Leveson et al. | |
| 4,804,839 A * | 2/1989 | Broadbent | G01N 30/7206 250/281 |
| 5,652,431 A | 7/1997 | DeSisto et al. | |
| 5,768,937 A | 6/1998 | Wajid et al. | |
| 6,169,370 B1 * | 1/2001 | Platzer | H05H 1/30 219/121.36 |
| 7,046,012 B2 | 5/2006 | Dean et al. | |

(Continued)

OTHER PUBLICATIONS

D. Shamiryan et al.; CRC Handbook of Chemistry and Physics 2004-2005; JANAF, 1985; 1 page.

(Continued)

*Primary Examiner* — Hugh H Maupin
(74) *Attorney, Agent, or Firm* — Barclay Damon LLP

(57) ABSTRACT

Systems for a managing a chemical process and photoionization detectors for analyzing a process gas are presented. In one aspect, the system includes a process gas source in fluid communication with the process chamber and a photoionization detector. The photoionization detector is configured to analyze the process gas. The photoionization detector includes a heat resistant coupling for connection to the system, a gas sample chamber with the radiation window soldered or brazed to a wall of the gas sample chamber, and a radiation source configured to emit radiation through the radiation window and into the gas sample chamber to analyze the process gas. In another aspect, the photoionization detector includes a removable coupling, a gas sample chamber, and a radiation source. The removable coupling is for connection to the process gas handling system and includes a metal gasket and metal flanges.

19 Claims, 4 Drawing Sheets

(56) References Cited

U.S. PATENT DOCUMENTS 7,373,257 B2 5/2008 Arno
2013/0214153 A1* 8/2013 Morrisroe ............. F23C 99/003
　　　　　　　　　　　　　　　　　　　　　250/288

OTHER PUBLICATIONS

Roland A. Levy; Final Report, Investigation of Chemically Vapor Deposited Tantalum for Medium Caliber Gun Barrel Protection, SERDP Project WP-1425; Oct. 2008; 43 pages.

* cited by examiner

PROCESS GAS MANAGEMENT SYSTEM AND PHOTOIONIZATION DETECTOR

CROSS-REFERENCE TO RELATED APPLICATION

This application claims priority to U.S. Provisional Patent Application Ser. No. 62/175,771, filed Jun. 15, 2015, and entitled PHOTOIONIZATION DETECTOR FOR USE IN INDUSTRIAL APPLICATIONS, the entirety of which is incorporated herein by reference.

BACKGROUND

The present disclosure relates to systems for transporting and/or analyzing gas mixtures, and more particularly, to gas transport and analysis systems with photoionization detectors. Many industrial processes, such as semiconductor processing and pharmaceutical drying processes include the transport of chemicals as gas species in carrier gas streams. In such processes, it is generally desirable to know various characteristics of the gas, such as the partial pressure of the gas species in the carrier stream, in order to validate that the characteristics of the chemicals in the carrier stream are at the required levels for the particular process.

For instance, the semiconductor industry makes use of many deposition processes in which gas species are transported by a carrier gas. Semiconductor fabrication processes such as metal organic chemical vapor deposition (MOCVD) and atomic layer deposition (ALD) each require the delivery of an organometallic precursor chemical at a particular partial pressure in a relatively inert carrier gas stream to a manufacturing process chamber. Control of the partial pressures of these precursors is often accomplished by relying on experimentally established recipes which are described, for example, in terms of pressures, temperatures, flows, durations, or other process characteristics. The instrumentation used to control such recipes can include temperature sensors, mass flowmeters, total pressure gauges, or other sensors. The actual amount of precursor materials being delivered to the process may be inferred from various measurements, and also controlled, for example, by adjustments to heater currents, flow control means, or other process parameters.

Some of these precursors are solids or liquids at room temperature, and are heated to establish the required partial pressures in the carrier gas as it passes through a precursor container. In these cases, it is also often necessary that the entire gas handling system be kept at elevated temperatures to prevent condensation of the precursor. All of the sensors used must tolerate the elevated temperatures required to prevent the precursor from condensing in the sensors themselves, as this would degrade the quality of the measurements being made and shorten the lifetimes of the sensors. Furthermore, as these sensors only measure total gas flow or total pressure of both species (precursor and carrier) in the stream, any change in the relative mixture amounts may go unnoticed. Changes that occur due to system faults such as failed heaters resulting in condensation of the precursor in the gas lines, or reduced evaporation of precursor due to decreasing surface area or channeling in the case of a solid precursor, or falling depth in the case of a liquid precursor, could be misinterpreted as changes in carrier flow, or overlooked altogether in the case of mixtures with low percentages of precursor.

Wajid et al. (U.S. Pat. No. 5,768,937) describes a system for measuring the makeup of a binary gas mixture of an MOCVD precursor in a carrier wherein the resonance frequency of an acoustic cell through which the binary mixture flows is measured. Since this frequency depends on the speed of sound in the gas that fills the cell, and as the speed of sound is directly related to the average molecular weight of the gas (as well as temperature and pressure), the composition of a mixture made up of two known components can be calculated based on knowledge of this resonance frequency. Such a system is somewhat complex, as it uses precision membranes as microphones and speakers, and requires tuned acoustic cavities with tight tolerances. Such systems also use elastomer or fluoroelastomer o-rings, and are prone to permeation of environmental gases through the o-rings and the outgassing of contaminants from the o-ring materials themselves, into the gas in the cell.

DeSisto et al. (U.S. Pat. No. 5,652,431) describes a sensor that measures the amount of metalorganic precursor in a gas stream wherein the gas stream flows through a UV-visible light absorption cell. UV-visible radiation enters the cell from one end and passes through some predetermined length of gas to the other end of the cell where it is collected. Some features of the spectral makeup of the collected radiation are then compared to those same features of the injected radiation, and the differences between them are indicative of the UV-vis absorption that can be attributed to the gas along the optical path. A similar system is described by Arno (U.S. Pat. No. 7,373,257 B2), except that rather than using UV-visible radiation, Arno describes measuring the partial pressure of precursors using the absorption by the gas mixture of different infrared wavelengths. Absorption based sensors require a large sensor size because the radiation must pass through a considerable amount of gas for accurate measurements to be obtained.

Leveson et al. (U.S. Pat. No. 4,413,185) describes the use of a photoionization detector in a gas chromatograph. Dean et al. (U.S. Pat. No. 7,046,012 B2) describes a photoionization detector used in a handheld environmental monitor. In both cases, the photoionization detector described comprises an ionization volume enclosed by insulating ionization chamber, often made of a dielectric such as a fluorocarbon-based plastic, with a plurality of electrodes positioned in the gas stream and in close proximity to the ionization process to enable collection of the ions that are made. The gas seals between the UV radiation sources in the photoionization detectors of the current art and their ionization chambers are made with either elastomer or fluoroelastomer o-rings or a tight fit through a hole in the ionization chamber. Such a photoionization detector is not suitable for use in high temperature environments.

Prior art sensors, such as those mentioned above, suffer from various limitations which make them inappropriate for use in certain applications, such as semiconductor processing or pharmaceutical drying. For instance, acoustic based sensors are incompatible with high temperature processing due the temperature sensitivity of their components. In addition, absorption based sensors typically require long lengths of transport gas to be analyzed, making them incompatible with the requirements of compact gas transport analyzers. Further, the sensors are also highly sensitive to the temperature of a process gas. As one example, the aforementioned sensors suffer from the limitation that the sensors themselves typically require materials of construction which make them incompatible with the high temperatures necessary for the transport of many modern organometallic precursors. As another example, speed of sound partial pressure sensors must account for the square root dependence of acoustic wave propagation on the temperature of the gas, thus mandating tight temperature control.

Many acoustic receivers and transmitters also have strong and complex temperature dependencies. Infrared detectors must be kept thermally isolated from heated gas paths and excluded from heated zones to avoid unacceptably high thermal noise. Many UV sources such as UV-diodes have very low optical efficiency, and thus these devices must sink large amounts of waste heat to operate over acceptable lifetimes. Maintaining a cool emitter is made more difficult in proximity to high temperature gas paths and can be much more expensive in the case where the entire sensor is intended to be installed in a high temperature zone and thus requiring active cooling.

By way of further background, photoionization detectors may be used to measure the partial pressure of gas species having relatively low ionization energies in the presence of other gas species with higher ionization energies. For example, a sample of the gas mixture being analyzed may pass through a flow cell, and some sub-volume of the gas may be exposed to UV radiation of an energy high enough to cause ionization of the target gas species to be detected, but low enough not to cause ionization of the other species in the mixture. This ionization produces a population of positive ions the density of which is proportional to the number density of the target gas species. The proportionality is related to the ionization cross section of the species along with various geometrical factors describing the intersection of photon flux through the interrogated sample volume, and factors affecting the lifetime of the ions, such as collisions with walls. This number density can be related to the partial pressure of the target species by temperature with an equation of state such as the ideal gas law. Beyond the positive ions, the ionization process also results in the generation of free electrons that were removed from the target species gas molecules by the ionization process. An appropriately biased collector electrode positioned inside of the cell can be made to collect either the ions or, alternatively, the electrons by the choice of electrical biasing. Measurement of the current on this collector electrode is then, in principle, representative of the partial pressure of the ionized species.

In a photoionization detector, the collected current is dependent not only on the partial pressure of the ionized species, but also on the pressure of all species present. This is due to collisions between the ions and the gas in the chamber, as well as reduction of UV photon penetration length into the gas. Non-linearity in the collected ion current due to change in total pressure can be corrected for by incorporating knowledge of the total pressure in the system obtained from a suitable pressure gauge.

Photoionization detection technology may be used in gas chromatography, where the chemicals to be measured elute from a chromatographic column at times that are dependent on the gas species. The technology may also be used in hand-held sensors for detecting the presence and measuring the amount of various chemicals in the environment for the sake of environmental protection, health and safety, and tracking leaks, among others applications. In such a case, the gas mixture being analyzed may be near or above atmospheric pressure, and gas seals on the photoionization detectors may be made using various elastomers or fluoroelastomers. The gas mixture that has been analyzed by the photoionization detector may be subsequently exhausted as waste. While these types of materials and seals are generally acceptable for use in the typical photoionization detector applications, they are not tolerable in, e.g., semiconductor processing and some pharmaceutical drying applications that are far less tolerant of leakage either into or out of the sensor.

SUMMARY

In one aspect, disclosed herein is a system for managing a chemical process, including analyzing a process gas. For instance, the system includes a process gas source in fluid communication with a process chamber and a photoionization detector. The photoionization detector is configured to analyze the process gas. The photoionization detector includes a heat resistant coupling for connection to the system, a gas sample chamber with the radiation window soldered or brazed to a wall of the gas sample chamber, and a radiation source configured to emit radiation through the radiation window and into the gas sample chamber to analyze the process gas.

In another aspect, a photoionization detector configured to analyze a process gas is disclosed. The photoionization detector includes a removable coupling, a gas sample chamber, and a radiation source. The removable coupling is for connection to the process gas handling system and includes a metal gasket and a metal flange. The gas sample chamber has a radiation window soldered or brazed to a wall thereof. The radiation source is configured to emit radiation through the radiation window and into the gas sample chamber to analyze the process gas.

In a further aspect, a system for managing a deposition process is disclosed. The system includes a process gas source, a deposition chamber, and a photoionization detector. The process gas source includes a heated precursor and a source of a carrier gas. The process gas includes the carrier gas and a precursor gas species. The deposition chamber is in fluid communication with the process gas source. The photoionization detector is configured to analyze the process gas. The photoionization detector includes a removable heat resistant coupling for connection to the system, a gas sample chamber, and a radiation source. The gas sample chamber has a radiation window soldered or brazed to a wall thereof. The radiation source is configured to emit radiation through the radiation window and into the gas sample chamber to determine a partial pressure of the precursor gas species of the process gas.

The above embodiments are exemplary only. Other embodiments are within the scope of the disclosed subject matter.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION

Figure 1:
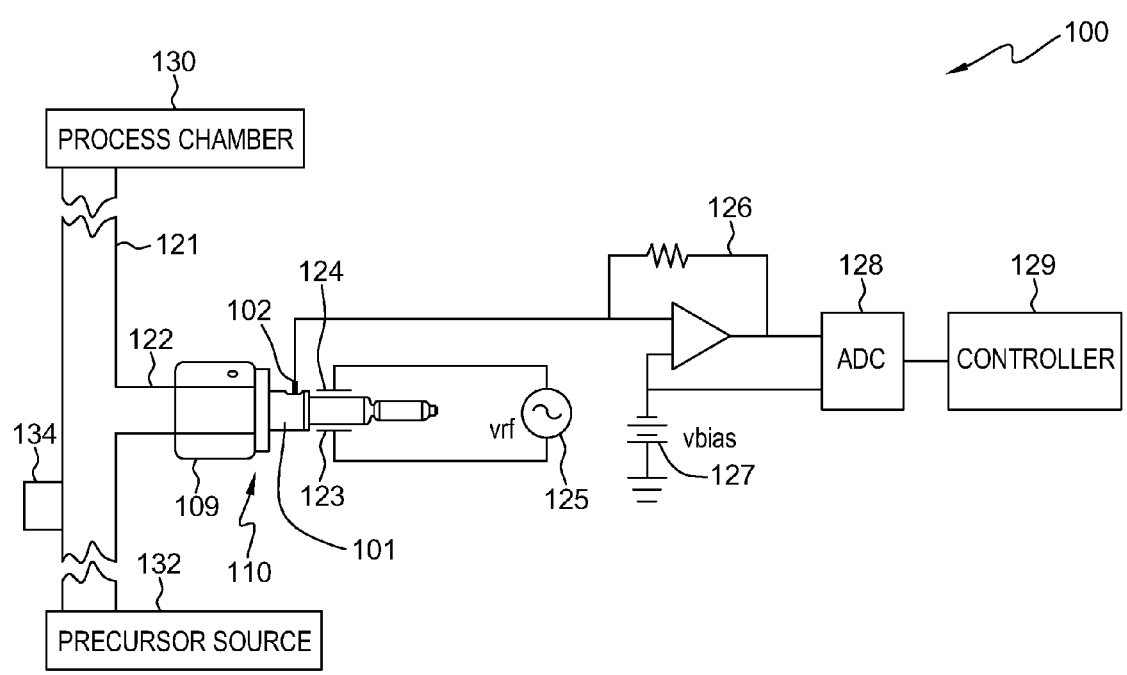
FIG. 1 is a diagram of an exemplary system for managing a chemical process including analyzing a process gas, in accordance with one or more aspects set forth herein.

The present disclosure provides, at least in part, a system for managing a chemical process including analyzing a gas and a photoionization detector, for use in, for example, high temperature environments, such as semiconductor processing or pharmaceutical drying applications. For example, the systems and photoionization detectors may be used to better understand and/or better control chemical processes in order to optimize production and utilization of material. In addition, the techniques disclosed herein may be used to design systems for various applications including gas handling, industrial processing, precursor or chemical source generation, process exhaust, or abatement. Further, such photoionization detectors may also be used for monitoring outgassing and verifying cleanliness in degas chambers or in the front opening universal pods (FOUPs) used to transport wafers between steps in a semiconductor manufacturing process.

Advantageously, the exemplary photoionization detectors and systems of the present disclosure include features which enable their use in high temperature and harsh environments typically encountered during semiconductor vapor deposition processes. For instance, the disclosed photoionization detector includes all metal seals which are capable of withstanding physical, chemical and thermal degradation during operation, while also offering field serviceability. As such, no hydrocarbon or fluorocarbon o-rings or gaskets are employed as seals in the photoionization detector or system. In addition, the systems are capable of in-line measurement of various physical characteristics of transported gas, such as partial pressure of various component gas species. Further, the particular configuration of the photoionization detectors enables deployment in high temperature spaces such as those typically found in a so-called hot box of a deposition apparatus. In addition, the electronics of the photoionization detector may be separated from the sensor portion so that the electronics may be protected from the high temperature environment where the sensor can be located. As another advantage, the disclosed photoionization technology allows for a relatively small-sized sensor which makes use of a relatively small volume of transport gas in conducting the measurements required, enabling deployment in narrow and tight spaces. As a further advantage, the photoionization detectors may be constructed using industry standard fittings so that they may be deployed in a variety of pre-existing environments. For example, vacuum coupling radiation (VCR), Swagelok or other compression fittings, or flanges, such as Conflat-style or quick flange (QF)-style flanges may be employed to provide an interface between the photoionization detector and the chemical process system. Such considerations allow for the removable photoionization detectors to tolerate high temperatures such as several hundred degrees Celsius, allowing for monitoring and managing of chemical processes such as atomic layer deposition precursor delivery systems. In addition, a removable photoionization detector allows for field replacement, for example, due to wearing out of the UV lamp. Alternate embodiments include a system with a fixed, non-removable photoionization detector.

By way of explanation, FIG. 1 is a diagram of an exemplary system 100 for managing a chemical process including analyzing a process gas, in accordance with one or more aspects set forth herein. The system 100 includes a photoionization detector 110 coupled to a gas transport line 121. The gas transport line 121 is configured to receive and deliver a process gas mixture from a precursor source 132 to a process chamber 130. In the illustrated example, a photoionization detector 110 has been disposed along gas transport line 121. In other examples, the photoionization detector 110 may be placed, for example, adjacent to or on the precursor source 132, on the process chamber 130, or on the system exhaust line either before or after any vacuum pumps used.

In one illustrative example of how the system of FIG. 1 may be used, a carrier gas may carry the precursor material from the precursor source 132 through the gas transport line 121 and into the process chamber 130. Such an example may be used in a deposition process, such as chemical vapor deposition (CVD) or atomic layer deposition (ALD). In another example, such as that of a pharmaceutical drying application, products may be placed in the process chamber 130 and heated so that solvents leave the products and are carried away by the gas transport line 121. The systems and detectors described herein may advantageously be used in high-temperature processes, such as metal organic chemical vapor deposition (MOCVD).

Returning now to FIG. 1 in detail, the photoionization detector 110 is used to monitor and manage the delivery of a precursor chemical species from the precursor source 132 to the process chamber 130. The photoionization detector 110 includes a removable heat resistant coupling 109. The removable heat resistant coupling 109 has been used to install the photoionization detector 110 to an inlet fitting 122 of the gas transport line 121. For example, the coupling implementation may be a vacuum coupling radiation (VCR) nut with a vacuum coupling radiation fitting. As used herein, a heat resistant coupling refers to, for example, a coupling that is capable of operation for its intended purpose (e.g., to allow analysis by the photoionization detector) at temperatures beyond the operating point of typical elastomers, such as beyond 100-300° C., or at metalorganic pyrolysis temperatures, such as approximately 400° C. for tantalum chloride.

The photoionization detector 110 includes the gas sample chamber 101. The gas sample chamber 101 includes a radiation window 105, for example, to the right-hand side of the gas sample chamber 101. A radiation source 106, such as a UV lamp, is configured to emit radiation through the radiation window 105 and into the gas sample chamber 101 to analyze the process gas. The radiation window 105 may be soldered or brazed to walls of the gas sample chamber 101. In addition, the components may be sealed and connected using metal-to-metal, glass-to-metal, or ceramic-to-metal interfaces, and/or glass-ceramic compression seals. Advantageously, photoionization detector 110 can withstand temperatures of several hundred degrees Celsius. For example, deployment near a precursor source at a temperature of greater than 350° C. may be achieved, in part, due to construction features such as the use of braze or solder-glass to hold radiation window 105 to the gas sample chamber 101 and the radiation source 106.

By way of explanation, during operation, a radiofrequency generator 125 delivers a high-voltage RF signal to electrodes 123, 124 near the radiation source 106 of the photoionization detector 101. This creates a plasma from the gas located inside the radiation source 106. This plasma in turn creates ultraviolet photons that are responsible for ionizing some of the gas molecules inside the gas sample chamber 101 of the photoionization detector 110.

Continuing with the operational explanation, the gas sample chamber 101 may be held at electrical ground, for example, through the coupling 109 to the gas transport line 121. The collector 102 may be biased negatively from ground by $V_{bias}$ supply 127 and current to-voltage-converter 126. In such a case the bias voltage on the collector 102, in concert with the sample chamber 101 being grounded, sets up an electric field that steers the ions created in the sample chamber 101 to the collector 102.

Next, the ion current, along with any leakage currents, is converted to a voltage difference at the input to the analog to digital converter (ADC) 128. Controller 129 monitors the output of the ADC 128, and may record or report ion currents, calculate equivalent partial pressures, may control radiofrequency generator 125, or may be used to control and manage the chemical deposition process by adjusting various process parameters. The controller 129 may include electronics for operation of the photoionization detector 110. The controller 129 may reside in a chassis removed from the photoionization detector 110. In such a case, the photoionization detector 110 may be connected to the controller 129 by a cable, or may be located directly adjacent to the photoionization detector 110. A configuration in which the photoionization detector 110 is separated from the controller 129 may allow for simplified operation at elevated detector temperatures, and a configuration in which the electronics and the controller 129 are located directly at the photoionization detector 110 may allow for more compact deployment. The controller 129 may make use of information obtained from photoionization detector 110 in order to control the chemical process. For example, various control parameters such as temperature, flow rate, valve states, or other measurements and sensor data may be used to control the process. In one specific example, the temperature of the drying process may be increased based on a detected low partial pressure being below a predetermined level of a solvent being dried out of a product. In another specific example, the temperature of a precursor source may be increased in order to facilitate a greater amount of the precursor gas species entering a carrier gas stream.

In one example, an electrical power source for running the radiation source 106 and/or measuring the detected signal current could be located at the photoionization detector 110. In another example, the electrical power source could be located remote to the photoionization detector 110, and may communicate there with by means of cabling. In another example, radiation source 106 may be a DC-type lamp with internal electrodes, or an AC type lamp driven by external electrodes. In a further example the electrodes may be built into a connector that slides over the radiation source 106 and a portion of a wall of the sample chamber 101. In such a case, the connector may also make connection to the collector 102. Further, signals may be brought to the lamp electrodes 123, 124 from a remotely located power supply and ion signals may be carried away from the photoionization detector 110 to remotely located measurement circuit. The remotely located measurement circuit may be used to determine information such as the partial pressure of the precursor or another chemical of interest, gas or precursor flow parameters, precursor temperature, etc.

The process gas, which may be a mixture, may include multiple gas species, such as for example, a first gas species and a second gas species. The photoionization detector 110 may be used to characterize a first gas species of the gas mixture transported by gas transport line 121. For example, the process gas may include a plurality of gas species and the photoionization detector 110 may be configured to measure the partial pressure or the chemical concentration of one of the plurality of gas species.

In addition, an additional sensor 134 may be disposed along the gas transport line 121. In such a case, the sensor 134 may be spaced apart from the photoionization detector 110. The controller 129 may receive data from both the photoionization detector 110 and the sensor 134, and process the data to obtain a measurement, such as the partial pressure of a precursor species of the gas mixture traveling in gas transport line 121.

Figure 2A:
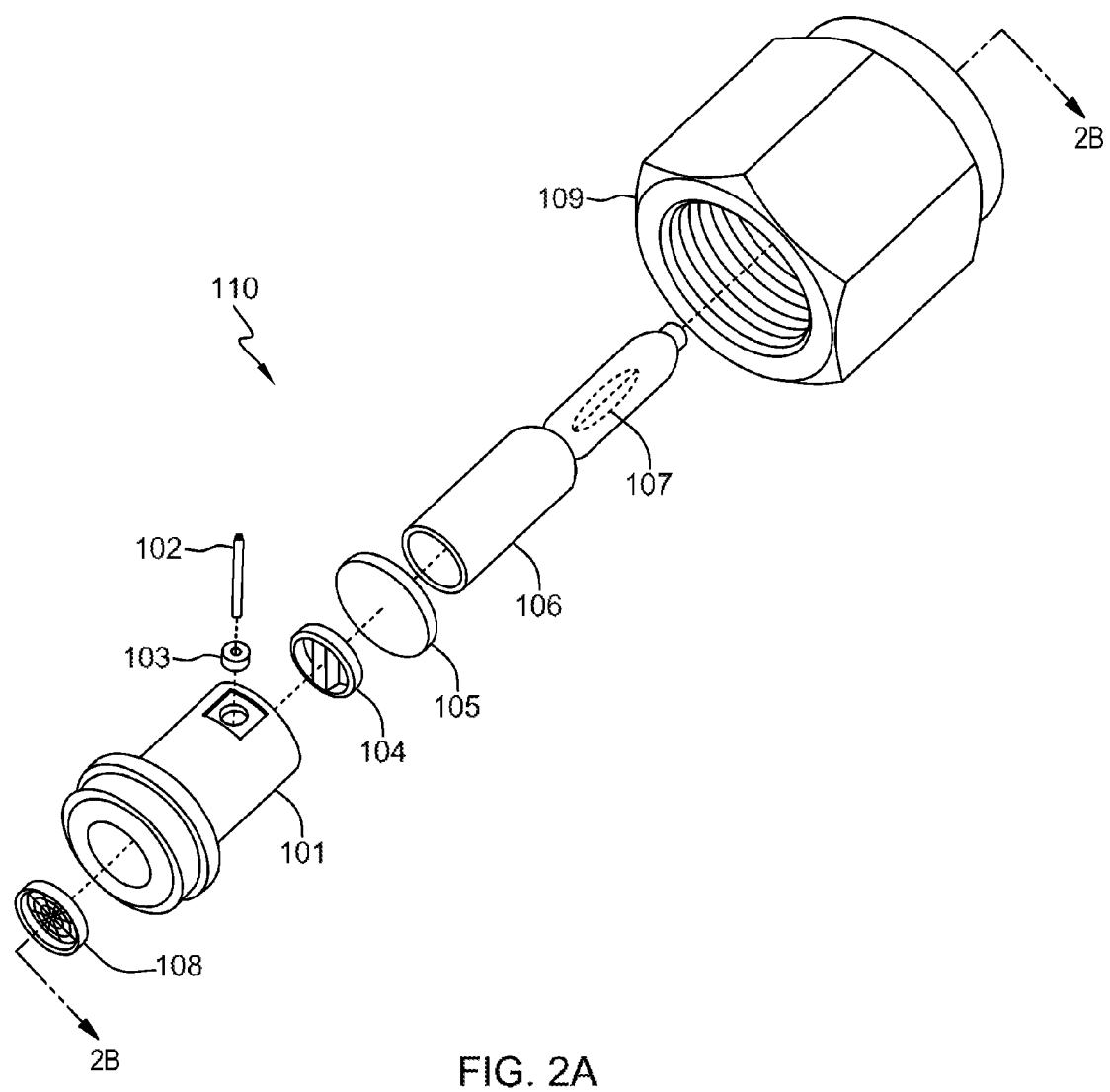
FIG. 2A is an exploded view of an exemplary photoionization detector, in accordance with one or more aspects set forth herein.
Figure 2B:
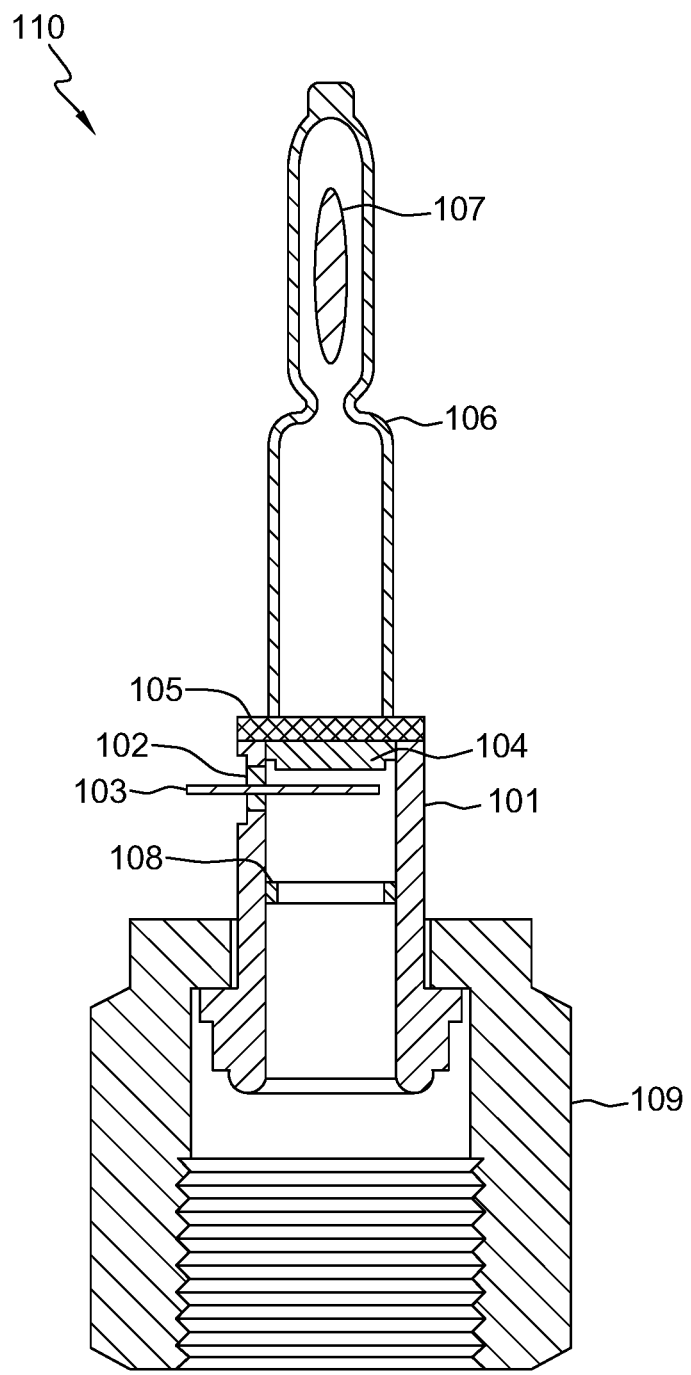
FIG. 2B is a cross-sectional elevational view of the exemplary photoionization detector of FIG. 2A, taken along line 2B-2B thereof, in accordance with one or more aspects set forth therein.

FIGS. 2A & 2B depict in detail the photoionization detector 110 of the system 100 (FIG. 1). FIG. 2A is an exploded view of the photoionization detector 110, and FIG. 2B is a cross-sectional elevational view of the photoionization detector 110 taken a long line 2B-2B of FIG. 2A. In the illustrated embodiment, the sample chamber 101 may be constructed from, for example, a vacuum coupling radiation gland, such as a ¼" VCR® gland made of 316 SS and having a profile at one that is designed to seal to a similar gland by crushing a metal gasket between the two glands when they are pulled up tight by means of mating threaded nuts. Advantageously, the use of all-metal sealing technology allows for use of the photoionization detector 110 in a gas handling system in which the use of elastomers and fluoro-elastomers are not tolerable, such as a high temperature deposition process, such as MOCVD.

In addition, sample chamber 101 may be formed by drilling and machining a metal gland to include various openings and features needed in the construction of the photoionization detector 110. For example, walls of the sample chamber 101 may be drilled to accept a conductive collector electrode or pin, in the form of the collector 102, from a direction essentially perpendicular to the axis of the photoionization detector 110. In addition the collector seal 103 may be included to hermetically seal the collector 102. The collector seal 103 can be made of a ceramic such as alumina, or a glass-ceramic, e.g., silicon oxide. The collector 102 can be made of stainless steel, nickel, or any other conductor that is tolerant of the processing steps described below and the chemicals being analyzed. The collector 102 and collector seal 103 can be sealed into the sample chamber 101 of the photoionization detector 110 using a metal braze, in the case of an alumina insulator, or a compression seal, in the case of a glass-ceramic. Either sealing method can provide an ultrahigh vacuum quality seal, and can be tolerant of the elevated operating temperatures required of most metalorganic precursor delivery systems. Also, either seal can provide a high level of electrical insulation. Advantageously, this prevents leakage currents between the collector 102 and the sample chamber 101 that might be inaccurately interpreted as ion currents. The length and positioning of the collector 102 should be such that it protrudes significantly into the sample chamber 101 defined by the inner walls of, e.g., a metal gland, but not so far as to touch the opposing side. In such a case, there is no direct contact between the collector 102 and any walls of the sample chamber 101.

Further, a shadow plate 104 may be deployed between the radiation source 106 and the collector 102. The shadow plate 104 shields the collector pin 102 from any energetic radiation that might cause electrons to be ejected from the collector pin 102 and be mistakenly measured as part of the current of interest. The shadow plate 104 is so named because it is positioned and shaped to put the collector pin 102 in its shadow and thus limit the number of photoelectrons likely to be ejected from the collector 102. After installation of the collector 102 and the collector seal 103 into sample chamber 101, and prior to the installation of the radiation window 105 and radiation source 106, shadow plate 104 can be installed into the end of the sample chamber 101, e.g., furthest from the gas handling system seal. This shadow plate 104 can also be made of stainless steel, nickel, or another process-compatible conductive material. For example, the shadow plate 104 may be made of a material that is easily resistance-welded to the inner wall of the sample chamber 101, although other means of holding the shadow plate 104 in place, such as screws or process-compatible adhesives, could be used. The shadow plate 104 may be shaped and positioned in the sample chamber 101 so as to allow significant passage of, e.g., UV radiation from the radiation source 106, e.g., a UV lamp, and window 105 to pass through and/or around it, but at the same time to prevent direct exposure of the collector 102 to the radiation. The purpose of preventing radiation leaving the radiation source 106 from striking the collector 102 is to reduce as much as possible the ejection of photoelectrons from the collector 102, which would subsequently be measured as an offset to the actual ion current, increasing noise on the useful signal and increasing the lower detection limit for the chemicals of interest.

Continuing with exemplary details of the assembly of photoionization detector 110, after installation of the shadow plate 104 the radiation window 105 and radiation source 106 can be installed. One having ordinary skill in the art will readily understand construction of UV lamps and the importance of material choices. In one embodiment, the radiation window 105 may be a UV-vis window and could be made of $MgF_2$ and the radiation source 106 could be a UV lamp made of borosilicate glass. Other examples of possible choices of UV-vis window materials include calcium fluoride and lithium fluoride. The choice of window material will depend on the photon energy required to ionize the target analyte, as well as compatibility with the process gases and temperatures. In one embodiment, the radiation window 105 is sealed to the sample chamber 101 on one side, and sealed to the lamp or radiation source 106 on its other side. Each of these seals could be made with appropriately chosen solders or brazes. In an exemplary embodiment, these seals are designed to be made at temperatures tolerable to the collector 102 and collector seal 103 described above. Once these solder joints are made, a getter 107 can be installed to help reduce the effects of any leakage on the lamp performance. The radiation source 106 or lamp is then evacuated and backfilled with a gas and closed off. The gas within radiation source 106 will make up the plasma which is the source of the UV photons during operation of photoionization detector 110. The choice of lamp gas is generally determined by the desired UV photon energies, Kr and Ar being two examples of gases often chosen.

In addition, a filter 108 can be installed in the sample chamber 101 between the collector 102 and the fitting or coupling end of the sample chamber that connects to the gas management and handling system to be monitored, for example, for connection to a gas transport line or directly to a process chamber or a precursor source. This filter 108 may be optionally used depending on the process being monitored. Advantageously, the filter 108 can protect the inner parts of the photoionization detector 110 from any particles that might be in the carrier gas stream that is being monitored. Also, should there be any particle-forming reactions in the sample chamber 101 of the photoionization detector 110 due to the presence of reactive species and the energetic radiation from the radiation source 106, the filter 108 would prevent any formed particles from being transported by the carrier gas from the photoionization detector 110 to the process being monitored. For example, some organometallic precursors may coat surfaces under UV illumination and could potentially flake off as particulates. In such a case, as a precaution, a filter 108 can be installed into the photoionization detector 110. This filter 108 should be chosen with holes or passages sized to forbid transport of particles that are big enough to cause problems in the process, but large enough to not limit gas flow unnecessarily. It could be, as examples, a metal or glass screen or frit, or metal or glass wool. For example, for MOCVD or ALD process monitoring applications, this filter may be selected as a sintered metal frit, a glass frit, a glass or metal wool, or an aluminum oxide plate with holes through it with, e.g., diameters on the order of $10^{-8}$ m. In addition, if an electrically non-conducting material is chosen for filter 108, an additional metal screen may be included between the filter 108 and the collector 102. This screen may be in electrical contact with the walls of the sample chamber 101 so that the electric fields which aid in ion collection by the collector 102 are not disturbed by the likely electrical charging of a non-conducting filter.

The filter 108 could be made of any material that is compatible with the process gases and tolerant of the required temperatures as long as the passages through it are of appropriate dimensions to let the process gases flow readily through and to prevent the passage of particles that are unacceptably large. The features of the filter 108 can be designed so that virtually all (e.g., 99.9999%) of particles larger than 100 nm are prevented from passing by the filter 108. The filter 108 can be designed to be highly tortuous to ensure that no light escapes through it, and that any metastable molecules or ions have a high probability of contacting a wall before exiting the photoionization detector 110.

By way of example, one exemplary system may be built with a gas sample chamber 101 constructed of a modified ¼" VCR® gland. In such a case, the coupling 109 may be built with a female VCR® nut to connect the photoionization detector 110 to the gas handling system being monitored. As noted in FIG. 2A, the coupling 109 may be installed on the photoionization detector 110 prior to other construction steps, or the coupling 109 may be modified to slide past the collector 102 so that it can be installed as the last step in the manufacturing process, or at installation time on the system being monitored. In different embodiments, different couplings may be employed. For example, a coupling may include a gland, a gasket, and a nut, or a coupling may include a female VCR nut, dependent upon the application.

In another example, prior to installing the radiation window 106, an intermediate transition ring (not shown) can be sealed to the sample chamber 101. This transition ring may include a material with a coefficient of thermal expansion intermediate to that of the sample chamber material and the radiation source or lamp material. Kovar can be used between stainless steel and borosilicate glass, because the Kovar may be welded to the stainless steel and soldered to the glass. For example, the radiation window 105 such as a UV-vis window may be sealed to the sample chamber 101, and the radiation source 106 or lamp may be sealed to the transition ring.

Figure 3:
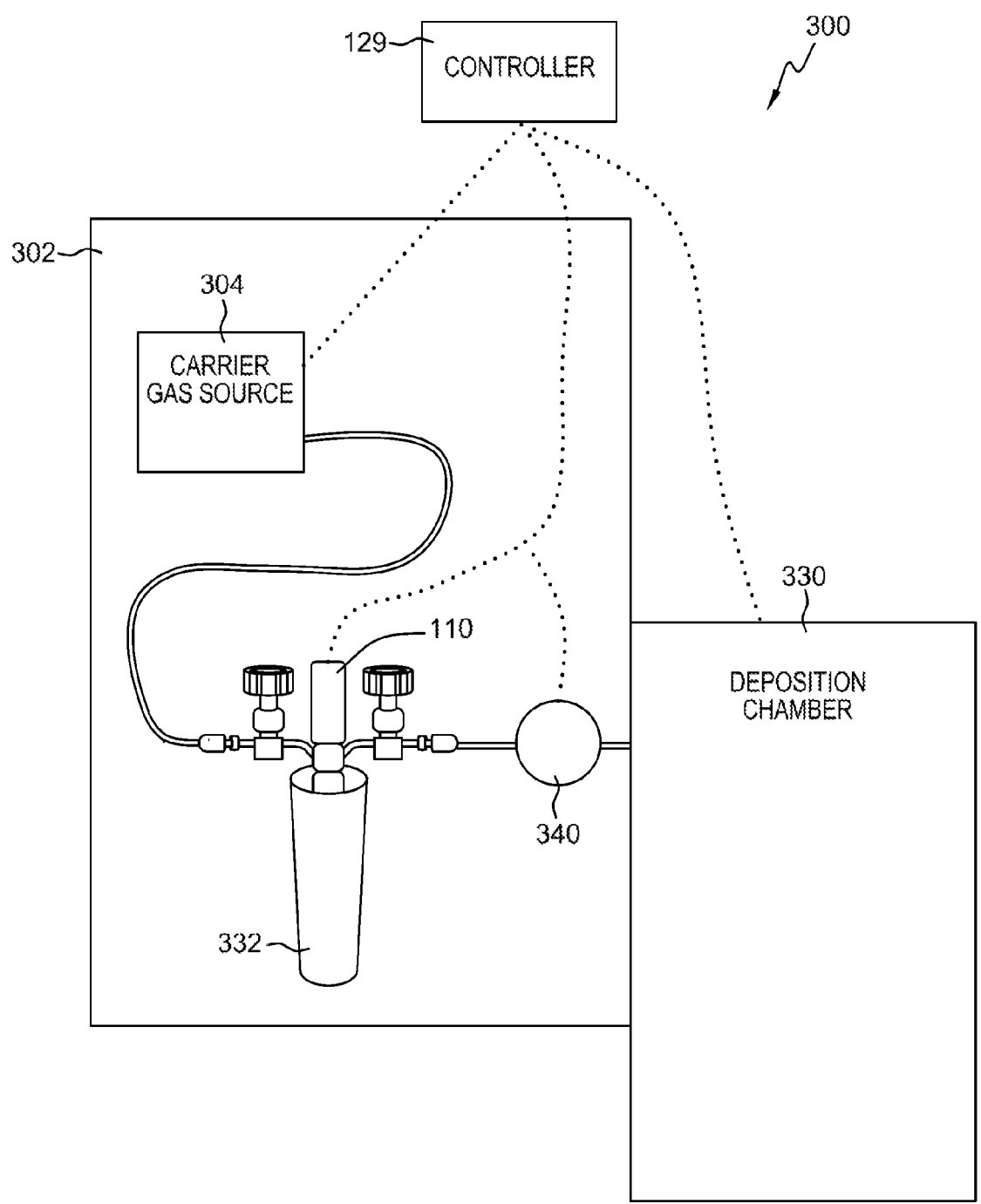
FIG. 3 is a diagram of an exemplary system for managing a deposition process, in accordance with one or more aspects set forth herein.

FIG. 3 is a diagram of a system 300 for managing a deposition process. Exemplary photoionization detector 110 is attached directly to a precursor source bottle 332, in a heated zone of gas cabinet 302. Controller 129 is installed in a separate box away from the gas cabinet 302, and is connected by electronics wiring to the different components, such as the carrier gas source 304, the photoionization detector 110, a valve 340, and the deposition chamber 330. In operation, the precursor source bottle 332 is heated to heat a precursor stored within, and a carrier gas source delivers carrier gas to the precursor source bottle 332. In one example, the controller 129 may ensure that a target partial pressure of the precursor gas species is present in the precursor source bottle 332 so that delivery of the process gas may be made to the deposition chamber 330 to achieve atomic later deposition on, for example, wafers within the deposition chamber 330, in such a way that wastage of the precursor is minimized. The controller 129 may control the temperature of the precursor source bottle 332, the flow rate of the carrier gas source 304, and the valve 342 achieve the target deposition rates within deposition chamber 330.

In order to further illustrate operation of the system 300 and photoionization detector 110, a specific process example of deposition of the tantalum film on a substrate is considered. Plasma enhanced atomic layer deposition (PEALD) of a tantalum film on a substrate may be achieved when the substrate is alternately exposed to pulses of gaseous tantalum pentachloride ($TaCl_5$) precursor in a carrier gas of argon, and pulses of atomic hydrogen derived from the cracking of molecular hydrogen by a plasma discharge. First, during the precursor pulse a self-limiting monolayer of $TaCl_5$ will cover the substrate surface. Next, the deposition chamber 330 is evacuated, and a pulse of atomic hydrogen then delivered to the chamber 330. The hydrogen reacts with the $TaCl_5$ on the surface of the substrate, producing HCl, which is subsequently pumped from the chamber 330. The combination of the first and second pulses leaves behind a thin, uniform tantalum film on the substrate. The two pulses may be repeated until the desired film thickness is achieved on the substrate surface. In this process, successful production of a good tantalum film will depend, among other things, on sufficient $TaCl_5$ being delivered to the surface during each precursor pulse. Economic success will require, among other things, that no more precursor is consumed than is necessary and that the process takes no more time than is necessary.

The precursor $TaCl_5$ is a moisture sensitive, crystalline solid at standard temperature and pressure. In one method of injecting $TaCl_5$ as a gas into the process chamber 330, the solid is placed into a stainless steel source bottle 332 which can be swept with a carrier gas (e.g., argon) and heated to a predetermined temperature. The flow rate of the carrier gas and the temperature of the precursor, as well as the specific geometries of the system and precursor will determine the amount of precursor that gets carried in any given amount of time out of the bottle 332 and into the process chamber 330 and to the substrate. In another method, carrier gas can enter the source bottle 332 at a predetermined pressure and remain at a predetermined temperature for a predetermined time so that the partial pressure of the $TaCl_5$ reaches its saturated vapor pressure. For example, the process may require a target pressure of several tens of mTorr of precursor for a duration of 1 second at the substrate in the process chamber 330 for the precursor pulse. To achieve this, the partial pressure in the source bottle 332 should be maintained such that the pulse carries sufficient precursor into the reaction chamber 330 to provide the target substrate exposure. This may accomplished by adjusting the source temperature. For example, if the volume of gas pulsed out of the source is only $\frac{1}{100}^{th}$ of the reaction chamber 330 volume, the pressure of precursor in the reactor chamber 330 will only be $\frac{1}{100}^{th}$ that of the source bottle 332. Therefore, for example, in order to achieve 30 mTorr of $TaCl_5$ in a process chamber 330, the precursor source bottle 332 may be held at a predetermined temperature for a predetermined time to achieve a source pressure of 3 Torr of $TaCl_5$. A vapor pressure curve for $TaCl_5$ would be readily available to one having ordinary skill in the art, and would show that 3 Torr of $TaCl_5$ may be achieved by holding the precursor source 332 at a temperature of around 140° C. Other surfaces of the system 300 that contact this precursor gas stream should be held at or above the temperature of the source bottle 332 in order to prevent precursor condensing out of the delivery stream.

Numerous difficulties arise when attempting to control a tantalum deposition process as described above. Advantageously, the photoionization detector 110 and system 300 disclosed herein can tolerate the high temperatures in the tantalum deposition process described above. As another advantage, the system 300 and photoionization detector 110 prevent intrusion of any outside gases from leaking or permeating into the system 300, due, in part, to the all-metal, glass-to-metal, and glass-ceramic compression sealing and the absence of elastomers, fluoroelastomers, hydrocarbons, and fluorocarbons in the construction. This allows successful deposition, because the precursors are sensitive to air components, particularly oxygen and water. In one deployment example, a photoionization detector 110 may be connected directly to a precursor delivery system or source bottle 332 using an industry standard fittings found on such a system. For example, a photoionization detector 110 may be connected at the source bottle 332 itself so that the partial pressure of precursor in the bottle 332 can be monitored and the temperature of the bottle 332 controlled to keep the desired partial pressure upstream of the pulse valve 340 (which may be used to control pulses of precursor gas entering the chamber). In such a case, because the photoionization detector 110 is located inside the "hot box" gas cabinet 302 that is typically used to heat the source bottle 332, the controller 129 and electronics may be located remotely outside of this hot box, and connected via electronics cables, to allow for operation of the system. Additionally, for monitoring some processes, e.g., ALD, it is advantageous to install the sensor in a position where it will only be exposed to one of the reactive species, in this case the precursor $TaCl_5$, and where it will not be exposed to the co-reagent, $H_2$ in the current example. This is to reduce the chances of metallization of the sensor's window and insulators, and to prevent fouling of the filter.

Continuing with the example of using precursor $TaCl_5$ and hydrogen pulses in the deposition of tantalum films, tantalum pentachloride's first ionization energy is at 11.08 eV. Therefore, a specific implementation of the photoionization detector 110 uses a LiF crystal UV-vis window and the lamp filled with argon so that the light from plasma struck in the lamp provides some fraction of the emitted radiation as photons with energy at 11.8 eV—high enough to ionize a representative sample of the precursor. In addition, RF power at 13 MHz may be used to drive the plasma, and may be supplied to the photoionization detector using a cable from outside of the hot box gas cabinet 302. In such an example, electrons removed from the precursor molecules by the UV photons are collected by the collector electrode, and the electron current is directly related to the number density of the precursor molecules in the volume illuminated by the UV lamp. Next, this electron current may be amplified by a preamplifier located in the sensor end of the cable, the amplified signal measured, and a corresponding partial pressure calculated. As noted above, the measurement and calculation may take place at the controller 129 electronics located outside of the hot box. Specifically, the partial pressure may be determined from the application of a calibration previously acquired for the intended precursor and the ideal gas law.

After calculation of the partial pressure, in order to optimize the deposition process to reduce waste and decrease processing time, the temperature of the source bottle 332 may be adjusted to maintain the desired partial pressure, or the pulse duration or pulse volume or carrier flow could be adjusted in response to the system calculations.

In another embodiment, photoionization detector 110 may be deployed to monitor exhaust from the deposition chamber 330. As mentioned above, after the step in which the substrate in the deposition chamber 330 is exposed to the precursor there is a step during which the unreacted precursor (and any reaction products) are pumped out of the deposition chamber 330. The photoionization detector 110 could be used to monitor this exhaust line and its output used to indicate that the deposition chamber 330 has been cleared of precursor.

In addition to semiconductor processing applications, another example of an industrial process in which it would be useful to measure the partial pressure of a particular chemical species in a carrier gas is in the manufacture of pharmaceuticals. Many pharmaceutical production processes include the delivery of some drug component in an organic solvent and the subsequent removal of the solvent by a drying process. These drying processes often include flowing a drying gas, such as nitrogen, at reduced pressure past the product. The solvent evaporates and enters the carrier stream and is subsequently pumped away with the carrier. A measurement of the partial pressure of solvent in this carrier stream would be an indication of the level of solvent removal achieved. As solvent removal, or drying, was completed the partial pressure of the solvent would decrease. The rate of drying depends on several parameters, including the morphology of the product material, the thickness and compactness of the products as it is loaded into drying boats, and the presence of a co-solvent such as water.

Typically, the endpoint for such a drying process is determined empirically through trial and error. In such cases, each batch must follow a preprogrammed drying program that is necessarily longer or hotter than optimum to ensure that the product will achieve an adequate level of dryness upon completion of the process step. This inefficiency results in increased operating costs, and in some instances may result in lost or otherwise damaged product.

Advantageously, the present disclosure provides for an in situ measure of the product's dryness, through use of photoionization detector 110 to analyze the process gas. As another advantage, measurement of the solvent partial pressure provides not only a tool for recipe optimization, but also for real-time control of the process. The present photoionization detector 110 is compatible with other requirements of sensors for pharmaceutical applications. This is because a typical requirement for the installment of sensors (such as for example temperature, or total pressure gauges) on a drying process in the pharmaceutical industry is that the sensor not outgas, be extremely leak-tight, and also be easily cleanable which often means resistant to chemicals such as ozone, hydrogen peroxide, steam, and other conditions used to sterilize the process chamber.

Further, the systems and photoionization detectors disclosed herein may be used to manage and monitor any chemical process in which a nominally closed system includes hydrocarbons or other species readily ionized by, for example, UV radiation, and not just processes in which gases are transported. For example, it would be useful to measure the partial pressure of a particular chemical species and manage the chemicals present inside front opening universal/unified pods (FOUPs) used to move wafers between manufacturing stages in semiconductor fabrication facilities.

Other variations and embodiments of the present systems and photoionization detectors may be used in different applications. In one example, a radiation window may be brazed into a system wall, for example a wall in a process gas chamber or in a precursor source. In another example, exhaust from semiconductor or other fabrication processing systems, such as scrubbers, may be monitored using these systems and photoionization detectors. In one implementation, a sample chamber wall may be grounded to act as an anode, and a cathode in its electrometer may be biased to collect positive ions created by the radiation in the sample gas. In another implementation, the photoionization detector may be deployed in a T-shaped gas transport line to analyze a flowing gas. In such a case a frit or other particle filter may be deployed on either or both of the upstream or downstream ends of the tee, with the ionization taking place between these ends.

This written description uses examples to disclose the invention, including the best mode, and also to enable any person skilled in the art to practice the invention, including making and using any devices or systems and performing any incorporated methods. The patentable scope of the invention may include other examples that occur to those skilled in the art.

What is claimed is:

1. A system for managing a chemical process including analyzing a process gas, the system comprising:
    a process gas source in fluid communication with a process chamber; and
    a photoionization detector configured to analyze the process gas, the photoionization detector comprising:
        a heat resistant coupling for connection to the process gas source of the system the heat resistant coupling being a removable coupling;
        a gas sample chamber with a radiation window soldered or brazed to a wall of the gas sample chamber, wherein the removable coupling provides a leak-tight gas connection between the source of the process gas and the gas sample chamber; and
        a radiation source configured to emit radiation through the radiation window and into the gas sample chamber to analyze the process gas.

2. The system of claim 1, wherein the process gas comprises a plurality of gas species and the photoionization detector is configured to measure a partial pressure of one of the plurality of gas species.

3. The system of claim 1, wherein the heat resistant coupling comprises a metal gasket and metal flanges.

4. The system of claim 1, further comprising a controller, the controller being configured to control an amount of the process gas delivered to the process chamber responsive to at least one control parameter.

5. The system of claim 1, further comprising a filter between the photoionization detector and the process gas source.

6. The system of claim 5, wherein the filter is configured to inhibit particulate reaction products of the process gas in the photoionization detector from leaving the photoionization detector.

7. The system of claim 1, wherein the process gas source heats a precursor, the process gas comprises the precursor and the photoionization detector is disposed adjacent to the process gas source.

8. The system of claim 7, wherein the chemical process comprises a chemical deposition process within the process chamber, the system is configured to transport the process gas with a carrier gas and the precursor to the process chamber, and the photoionization detector is configured to control the chemical deposition process.

9. The system of claim 1, wherein the chemical process comprises a drying process for removing a chemical species from a product within the process chamber, the system is configured to transport the chemical species away from the process chamber, and the photoionization detector is configured to control the drying process.

10. A photoionization detector configured to analyze a process gas, the photoionization detector comprising:
    a removable coupling for connection to a source of the process gas, the removable coupling comprising a metal gasket and metal flanges;
    a gas sample chamber with a radiation window soldered or brazed to a wall of the gas sample chamber, wherein the metal gasket and the metal flanges of the removable coupling provide a leak-tight gas connection between the source of the process gas and the gas sample chamber; and
    a radiation source configured to emit radiation through the radiation window and into the gas sample chamber to analyze the process gas.

11. The photoionization detector of claim 10, wherein the process gas comprises a plurality of gas species and the photoionization detector is configured to measure a partial pressure of one of the plurality of gas species.

12. The photoionization detector of claim 10, further comprising a collector for measuring a sample gas current, the collector extending into the gas sample chamber through a wall thereof, wherein the collector is sealed to the wall of the gas sample chamber using soldering, brazing or compression sealing.

13. The photoionization detector of claim 10, further comprising a filter disposed proximal to the removable coupling of the gas sample chamber.

14. The photoionization detector of claim 13, wherein the filter is configured to inhibit particulate reaction products of the process gas in the photoionization detector from leaving the photoionization detector.

15. The photoionization detector of claim 13, wherein the filter inhibits particles in the process gas from entering the photoionization detector.

16. The photoionization detector of claim 13, wherein the filter comprises a perforated aluminum oxide filter.

17. The photoionization detector of claim 13, wherein the filter comprises a sintered frit.

18. A system for managing a deposition process including analyzing a process gas, the system comprising:
    a process gas source, the process gas source comprising a heated precursor and a source of a carrier gas, wherein the process gas comprises the carrier gas and a precursor gas species; and
    a deposition chamber for the deposition process, deposition chamber being in fluid communication with the process gas source;
    a photoionization detector configured to analyze the process gas, the photoionization detector comprising:
        a removable heat resistant coupling for connection to the system, wherein the removable heat resistant coupling is configured to operate at temperatures above 300° C.;
        a gas sample chamber with a radiation window soldered or brazed to a wall of the gas sample chamber, wherein the removable heat resistant coupling provides a leak-tight gas connection between the source of the process gas and the gas sample chamber; and
        a radiation source configured to emit radiation through the radiation window and into the gas sample chamber to determine a partial pressure of the precursor gas species of the process gas.

19. The system of claim 18, further comprising a filter between the photoionization detector and the process gas source, wherein the filter is configured to inhibit particulate reaction products of the precursor gas species in the photoionization detector from leaving the photoionization detector.

* * * * *